(12) United States Patent
Rutt et al.

(10) Patent No.: US 11,213,048 B2
(45) Date of Patent: Jan. 4, 2022

(54) PROTEIN RICH FOOD INGREDIENT FROM BIOMASS AND METHODS OF PREPARATION

(71) Applicant: SMALLFOOD, INC., Halifax (CA)

(72) Inventors: George C. Rutt, San Diego, CA (US); James H. Flatt, Colorado Springs, CO (US); Peter Domaille, San Diego, CA (US); Gerardo V. Toledo, Belmont, MA (US)

(73) Assignee: Smallfood, Inc., Halifax (CA)

( * ) Notice: Subject to any disclaimer, the term of this patent is extended or adjusted under 35 U.S.C. 154(b) by 0 days.

(21) Appl. No.: 14/809,051

(22) Filed: Jul. 24, 2015

(65) Prior Publication Data

US 2017/0020159 A1    Jan. 26, 2017
US 2017/0196238 A9    Jul. 13, 2017

Related U.S. Application Data

(60) Provisional application No. 62/029,324, filed on Jul. 25, 2014.

(51) Int. Cl.
| | | |
|---|---|---|
| A23L 7/135 | (2016.01) | |
| A23J 1/00 | (2006.01) | |
| C07K 14/405 | (2006.01) | |
| A23K 20/147 | (2016.01) | |
| A23L 33/195 | (2016.01) | |

(52) U.S. Cl.
CPC ............. *A23J 1/009* (2013.01); *A23J 1/008* (2013.01); *A23K 20/147* (2016.05); *A23L 7/135* (2016.08); *A23L 33/195* (2016.08); *C07K 14/405* (2013.01); *A23V 2002/00* (2013.01)

(58) Field of Classification Search
CPC .... A23J 1/09; A23J 1/008; A23J 1/009; A34J 1/009; C07K 14/405; A23K 20/147; A23L 7/135; A23L 33/195; A23V 2002/00
USPC .................................................. 426/634, 49
See application file for complete search history.

(56) References Cited

U.S. PATENT DOCUMENTS

| | | | |
|---|---|---|---|
| 3,197,309 A | 7/1965 | Chapman et al. | |
| 5,130,242 A | 7/1992 | Barclay | |
| 8,084,038 B2 | 12/2011 | Kale | |
| 8,197,691 B2 | 6/2012 | Kale | |
| 8,318,019 B2 | 11/2012 | Kale | |
| 8,323,501 B2 | 12/2012 | Kale | |
| 8,475,660 B2 | 7/2013 | Kale | |
| 8,551,336 B2 | 10/2013 | Kale | |
| 8,552,160 B2 | 10/2013 | Kale | |
| 8,658,772 B2 | 2/2014 | Kale | |
| 8,748,588 B2 | 6/2014 | Kale | |
| 2004/0058051 A1 | 3/2004 | Yunusov et al. | |
| 2005/0186312 A1 | 8/2005 | Loh et al. | |
| 2006/0198938 A1 | 9/2006 | Chen et al. | |
| 2010/0233760 A1 | 9/2010 | Apt | |
| 2010/0239712 A1 | 9/2010 | Brooks et al. | |
| 2010/0260887 A1 | 10/2010 | Ufaz et al. | |
| 2010/0303990 A1 | 12/2010 | Brooks et al. | |
| 2011/0086386 A1 | 4/2011 | Czartoski | |
| 2011/0256282 A1 | 10/2011 | Piechocki et al. | |
| 2011/0274797 A1 | 11/2011 | Segall et al. | |
| 2011/0319596 A1 | 12/2011 | De La Torre-Montemayor | |
| 2012/0021457 A1 | 1/2012 | Tang | |
| 2012/0035348 A1 | 2/2012 | Kale | |
| 2012/0053327 A1 | 3/2012 | Kale | |
| 2012/0128851 A1* | 5/2012 | Brooks .................. | A21D 2/165 426/541 |
| 2012/0258236 A1 | 10/2012 | Cruz et al. | |
| 2013/0017594 A1 | 1/2013 | Raney et al. | |
| 2013/0122180 A1 | 5/2013 | Brooks et al. | |
| 2013/0142905 A1 | 6/2013 | Gibbons et al. | |
| 2014/0005422 A1 | 1/2014 | Kale | |
| 2015/0201649 A1 | 7/2015 | Lei | |
| 2016/0183565 A1 | 6/2016 | Rudinger et al. | |
| 2016/0340640 A1 | 11/2016 | Macquart et al. | |
| 2018/0208886 A1 | 7/2018 | Cagnac et al. | |

FOREIGN PATENT DOCUMENTS

| | | |
|---|---|---|
| CN | 101 429 467 A | 5/2009 |
| CN | 102020705 B | 8/2012 |
| CN | 103748104 A | 4/2014 |
| EP | 1 433 463 B1 | 9/2010 |
| WO | WO 2011/057406 A1 | 5/2011 |
| WO | WO 2011/130578 A2 | 10/2011 |
| WO | WO 2012/049503 A1 | 4/2012 |
| WO | WO 2014/015000 | 1/2014 |

(Continued)

OTHER PUBLICATIONS

Ross, A. B. et al. J. Anal. Appl. Pyrolysis 85: 3-10 (2009) (Year: 2009).*
Szabo, N. J. et al. Food and Chem. Toxicoloty. 65:301-311 (2014) (Year: 2014).*
International Search Report dated Apr. 8, 2016, regarding PCT/US2016/014725, pp. 1-28.
International Search Report dated Oct. 30, 2015, regarding PCT/US2015/042113, pp. 1-9.
Extended European Search Report dated Nov. 14, 2017, regarding EP 15 82 5225, pp. 1-14.
Database WP I, Week 201150, Thomson Scientific, London, GB; AN 2011-G00165, XP002791852, & CN 102 020 705 A (Univ Yangtze) Apr. 20, 2011.

(Continued)

*Primary Examiner* — Hamid R Badr
(74) *Attorney, Agent, or Firm* — DLA Piper LLP (US)

(57) ABSTRACT

The present invention provides a protein material and food ingredient from a sustainable and stable source. The sustainable and stable source of the food or food ingredient is biomass, for example an algal or microbial biomass. The invention discloses that the biomass can be subjected to a series of steps to derive the protein material and food or food ingredient, which has high nutritional content without the unacceptable organoleptic properties that typically accompany proteins and food ingredients from these sources.

4 Claims, 1 Drawing Sheet

(56) References Cited

FOREIGN PATENT DOCUMENTS

| WO | WO 2014/046543 A1 | 3/2014 |
|----|----|----|
| WO | WO 2014/199220 A1 | 12/2014 |
| WO | WO 2015/011418 A1 | 1/2015 |
| WO | WO 2015/107312 | 7/2015 |
| WO | WO2015150716 A2 | 10/2015 |
| WO | WO 2016/015013 A1 | 1/2016 |
| WO | WO 2017/012931 | 1/2017 |

OTHER PUBLICATIONS

International Search Report dated Apr. 14, 2017, regarding PCT/US2017/015177.
Pitchford, Paul: "Chlorella: A Nutrient-Rich Algae"; Chlorella Facts, NaturoDoc, 2012, pp. 1-7.
Supplementary Partial European Search Report dated Jun. 17, 2019, regarding EP 17 74 4909.
Gerde, Jose A. et al: "*Optimizing protein isolation from defatted and non-defatted Nannochloropsis microalgae biomass*", Algal Research, 2013, vol. 2, pp. 145-153.
Japanese Office Action dated May 23, 2019, regarding JP 2017-504026.
Nakazawa, Atsushi et al.: "*Optimization of biomass and fatty acid production by Aurantiochytriou* sp. *Strain 4W-1b*"; Pocedia Environmental Sci., 15: 2012, 27-33.
Lin, Jiaping et al.: "*Preparation and Evaluation of the Chelating Nanocomposite Fabricated with Marine Algae Schizochytrium* sp. *Protein Hydrolysate and Calcium*"; J. Agric. Food Chem., 2015, 63, 44, 9704-9714.
JP Office Action in Japanese Application No. 2018-539156, dated Sep. 17, 2020, 8 pages (with English translation).
EP Office Action in European Application No. 17744909.7, dated Nov. 18, 2020, 5 pages.

* cited by examiner

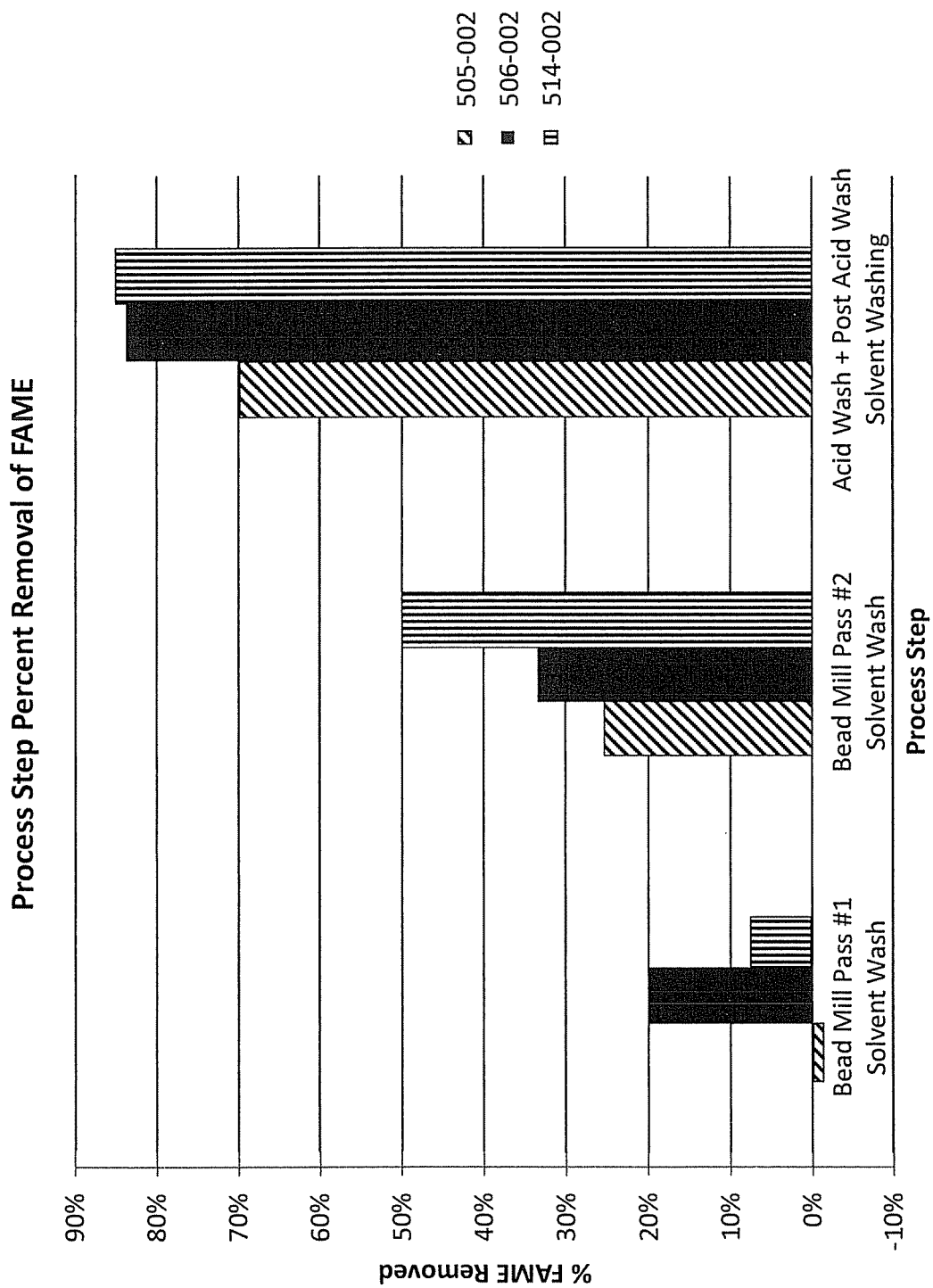

PROTEIN RICH FOOD INGREDIENT FROM BIOMASS AND METHODS OF PREPARATION

This application claims the benefit of U.S. provisional application No. 62/029,324, filed. Jul. 25, 2014, which is hereby incorporated by reference in its entirety, including all Tables, Figures, and Claims.

BACKGROUND

Proteins are essential nutritional components and protein rich material is often added to various types of food products in order to increase the nutritional content. Current sources of protein material include various grains and animal sources, but their availability is often subject to wide seasonal fluctuations, limiting their commercial use by food manufacturers. Grain based solutions for protein production also consume a large amount of productive land and water resources that might otherwise be better utilized. These sources are also limited in their ability to supply sustainable supplies of proteins in the quantities necessary. Additional and more reliable sources of proteins are needed to supply both a growing humanity and as feed for domestic animals.

Algal and microbial sources of proteins or other nutritional materials have great potential and would be highly desirable as they can reduce seasonal fluctuations and nevertheless provide a consistent, economic, and sustainable source of nutritional materials to food providers. Proteins and other nutritional materials produced by these sources could be used to supplement cereals, snack bars, and a wide variety of other food products. Furthermore, if organisms dependent on photosynthesis for energy (e.g., algae) could be made to produce useable proteins, it would have a highly favorable effect on the energy equation in food production.

However, algal and microbial sources of proteins often suffer from significant disadvantages in that they contain substances that are severely displeasing in terms of their organoleptic taste and smell properties. It would be highly advantageous to be able to harvest proteins from algal and microbial organisms that do not have the displeasing organoleptic properties. Such proteins would be very useful as foods, food ingredients, and nutritional supplements.

SUMMARY OF THE INVENTION

The present invention provides a proteinaceous food or food ingredient from a sustainable, economic, and stable source, and methods for obtaining same. In different embodiments the sources of the proteinaceous food ingredient are biomass sources, such as algal and microbial organisms. In different embodiments algae, microbial biomass, algal biomass, or kelp can be utilized as such sources. The invention discloses that the biomass can be subjected to a series of steps to derive a protein material that has high protein nutritional content and without the undesirable organoleptic taste and smell properties that typically accompany biomass from these sources. The steps include exposing the biomass to a depressed pH.

In a first aspect the invention provides methods of producing a protein material. The methods involve exposing a delipidated biomass that contains a proto-protein to acidic conditions by adjusting the pH of the biomass to a depressed pH of less than 4.5 and holding the pH of the biomass at said depressed pH for at least 10 minutes to convert the proto-protein into the protein material. In one embodiment the pH of the biomass can be adjusted to a depressed pH of less than 4.0 and the pH of the biomass is held at said depressed pH for about 30 minutes, but in other embodiments the pH of the biomass is adjusted to about 3.5 and the pH is held for about 30 minutes. In one embodiment after adjusting the pH to the depressed pH of less than 4.0 the pH is adjusted to a raised pH of greater than 4.0, but in another embodiment after adjusting the pH to the depressed pH of less than 4.0 the pH is adjusted to a raised pH of about 4.5.

The biomass can be exposed to the acidic conditions by contacting the biomass with an inorganic acid, which in various embodiments can be sulfuric acid or hydrochloric acid. The biomass can be delipidated by subjecting it to mechanical homogenization while in contact with a solvent. The solvent can be selected from the group consisting of: ethyl alcohol, isopropyl alcohol, and a mixture of hexane and acetone. In any embodiment the biomass can be algal biomass.

In another aspect the invention provides methods of making a food product by combining the protein material produced by a method of the invention with a foodstuff to make said food product. The food product can be a breakfast cereal, a snack bar, a soup or stew, a nutrition bar, a binder for bulk artificial meats, or an artificial cheese. The food produce can also be animal feed.

In some embodiments less than 25% of the proto-protein molecules have a molecular weight of below 15,000 daltons. The methods of the invention can also decreases the ratio of arginine, glutamic acid (or glutamic acid and glutamine), or hydroxyproline comprised in the protein material relative to the ratio in the delipidated biomass. The methods can also involve a step of centrifugation and the production of a centrifugation pellet and supernatant, which can be done after the exposure to acidic conditions, and wherein the ratio of arginine in the pellet/supernatant is less than 1.0 and/or wherein ratio of glutamic acid in the pellet/supernatant is less than 1.0.

In another aspect the invention provides a food ingredient containing a protein material derived from biomass by exposing the biomass to acidic conditions the protein material having at least 65% protein content (w/w); less than 6% lipid content (w/w); and less than 8% ash content. The lipids can be fatty acids, and the fatty acids can be polyunsaturated fatty acids. The food ingredient can be derived from algal biomass. The food ingredient can contains at least 75% protein w/w and less than 5% lipid content w/w. The food ingredient can be present in the form of a powder.

In another aspect the invention provides methods of improving the hedonic properties of a protein containing composition by subjecting the protein containing composition to a method of the present invention.

DESCRIPTION OF THE FIGURES

FIG. 1 is a bar graph illustrating the removal of lipidic material at steps of a process of the invention.

DETAILED DESCRIPTION OF THE INVENTION

The invention provides a stable and sustainable source of a proteinaceous food ingredient, with the source being biomass produced by phototrophic and/or heterotrophic algae or microbes such as, for example, microbial biomass, algal biomass, algae, kelp, and seaweed. The organisms can be either single cellular or multi-cellular organisms. These sources have great potential as a stable and sustainable source of proteinaceous food ingredients. The invention therefore discloses protein materials useful as food, food ingredients, or food supplements and which have high nutritional value and acceptable or pleasing organoleptic taste and smell properties. Also disclosed are methods of manufacturing the food ingredients and methods of manufacturing food products containing a food ingredient of the invention.

The invention provides a proteinaceous food or food ingredient containing a protein content of at least 50% or at least 60% or at least 65% or at least 68% or at least 70% or at least 72% or at least 75% or at least 78% or at least 80% or at least 85% or at least 90%, or from 50% to 70%, or from 65% to 75%, or from 70% to 80%, or from 70% to 85%, or from 70% to 90%, or from 75% to 90%, or from 80% to 100%, or from 90% to 100%, all w/w. In various embodiments the food or food ingredient contains all amino acids essential for humans and/or domestic animals and/or pets. In some examples the animals can be cattle, swine, horses, turkeys, chickens, fish, or dogs and cats.

The proteinaceous food or food ingredient can have varied lipid content such as, for example, about 5% lipid or about 6% lipid or about 7% lipid, or about 8% lipid or less than 8% or less than 7% or less than 6% or less than 5% lipid or less than 4% lipid or less than 3% lipid or less than 2% lipid or less than 1% lipid or from about 1% to about 5% lipid or from 2% to about 4% lipid. In different embodiments non-protein nitrogen content can be less than 12% or less than 10% or less than 8% or less than 7% or less than 6% or less than 5% or less than 4% or less than 3% or less than 2% or less than 1% or from about 1% to about 7% or from 2% to about 6% in the proteinaceous food or food ingredient. In a particular embodiment the food or food ingredient contains at least 80% protein w/w and less than 5% lipid w/w. The lipid content of the proteinaceous food or food ingredient can be manipulated as explained herein depending on the source of the protein material and the uses of the protein material to be produced, as well as by varying the steps in its production. The lipid content in the food or food ingredient can be provided, either partially or completely, by polyunsaturated fatty acids. The polyunsaturated fatty acids can be any one or more of gamma-linolenic acid, alpha-linolenic acid, linoleic acid, stearidonic acid, eicosapentaenoic acid, docosahexaenoic acid (DHA), and arachiconic acid, in any combinations. In any of the compositions the ash content can be less than 10% or less than 9% or less than 8% w/w.

The protein material of the invention can be utilized in a wide variety of foods. It can be used either as a supplement or a food substitute. As examples, the protein material can be utilized or incorporated within cereals (e.g. breakfast cereals containing mostly grain content), snack bars (a bar-shaped snack containing mostly proteins and carbohydrates), nutritional or energy bars (a bar-shaped food intended to supply nutrients and/or boost physical energy, typically containing a combination of fats, carbohydrates, proteins, vitamins, and minerals), canned or dried soups or stews (soup: meat or vegetables or a combination thereof, often cooked in water; stew: similar to soup but with less water and cooked at lower temperature than soup), as a binder for bulk and/or artificial meats (artificial meats are protein rich foods, usually based on soy or plant proteins, but having no real meat of animal origin in them, but they have characteristics associated with meat of animal origin), cheese substitutes, vegetable "burgers", animal or pet feed (e.g. in animal or livestock feed for consumption by domestic animals and/or pets—these feeds can be mostly grain products), and much more. It can also be a nutritional supplement such as a protein or vegetable protein powder. The protein material can also be converted into a food ingredient, e.g., a protein rich powder useful as a substitute for grain-based flour. The protein materials are useful as food ingredients or as foods for both human and animal consumers. In addition to providing an advantageous source of protein the proteinaceous material of the invention can also provide other nutrients, such as lipids (e.g., omega-3 and/or omega-6 fatty acids), fiber, a variety of micronutrients, B vitamins, iron, and other minerals being only some examples.

The algal or microbial organisms that are useful in producing the biomass from which the protein material of the invention is obtained can be varied and can be any algae or microbe that produces a desired protein-containing product. In some embodiments the organisms can be algae (including those classified as "chytrids"), microalgae, Cyanobacteria, kelp, or seaweed. The organisms can be either naturally occurring or can be engineered to increase protein content or to have some other desirable characteristic. In particular embodiments microbial or algal sources are utilized. In different embodiments algae and/or cyanobacteria, kelp, and seaweed of many genera and species can be used, with only some examples being those of the genera *Arthrospira*, *Spirulina*, *Coelastrum* (e.g., *proboscideum*), macro algae such as those of the genus *Palmaria* (e.g., *palmata*) (also called Dulse), *Porphyra* (Sleabhac), *Phaeophyceae*, *Rhodophyceae*, *Chlorophyceae*, *Cyanobacteria*, *Bacillariophyta*, and *Dinophyceae*. The alga can be microalga (phytoplankton, microphytes, planktonic algae) or macroalga. Examples of microalga useful in the invention include, but are not limited to, *Achnanthes*, *Amphiprora*, *Amphora*, *Ankistrodesmus*, *Asteromonas*, *Boekelovia*, *Bolidomonas*, *Borodinella*, *Botrydium*, *Botryococcus*, *Bracteococcus*, *Chaetoceros*, *Carteria*, *Chlamydomonas*, *Chlorococcum*, *Chlorogonium*, *Chlorella*, *Chroomonas*, *Chrysosphaera*, *Cricosphaera*, *Crypthecodinium*, *Cryptomonas*, *Cyclotella*, *Dunaliella*, *Ellipsoidon*, *Emiliania*, *Eremosphaera*, *Ernodesmius*, *Euglena*, *Eustigmatos*, *Franceia*, *Fragilaria*, *Fragilariopsis*, *Gloeothamnion*, *Haematococcus* (e.g., *pluvialis*), *Halocafeteria*, *Hantzschia*, *Heterosigma*, *Hymenomonas*, *Isochrysis*, *Lepocinclis*, *Micractinium*, *Monodus*, *Monoraphidium*, *Nannochloris*, *Nannochloropsis*, *Navicula*, *Neochloris*, *Nephrochloris*, *Nephroselmis*, *Nitzschia*, *Ochromonas*, *Oedogonium*, *Oocystis*, *Ostreococcus*, *Parachlorella*, *Parietochloris*, *Pascheria*, *Pavlova*, *Pelagomonas*, *Phceodactylum*, *Phagus*, *Picochlorum*, *Platymonas*, *Pleurochrysis*, *Pleurococcus*, *Porphyridium*, *Prototheca*, *Pseudochlorella*, *Pseudoneochloris*, *Pseudostaurastrum*, *Pyramimonas*, *Pyrobotrys*, *Scenedesmus* (e.g., *obliquus*), *Schizochlamydella*, *Skeletonema*, *Spyrogyra*, *Stichococcus*, *Tetrachlorella*, *Tetraselmis*, *Thalassiosira*, *Tribonema*, *Vaucheria*, *Viridiella*, *Vischeria*, and *Volvox*.

The algal or microbial organisms can also be chytrids, including but not limited to members of the genera *Aplanochytrium*, *Aurantiochytrium*, *Botryochytrium*, *Diplophrys*, *Japanochytrium*, *Labrinthulomycetes*, *Labryinthula*, *Labryinthuloides*, *Schizochytrium*, *Oblongochytrium*, *Thraustochytrium*, and *Ulkenia*. For the purposes of this invention all of the aforementioned organisms, including the chytrids, are considered "algae" and produce "algal biomass" when fermented or cultured. But any cells or organisms that produce a microbial biomass that includes a desired protein can be utilized in the invention.

In still further embodiments the microbial organism can be oleaginous yeast including, but not limited to, *Candida*, *Cryptococcus*, *Lipomyces*, *Mortierella*, *Rhodosporidium*, *Rhodotortula*, *Trichosporon*, or *Yarrowia*. But many other types of algae, cyanobacteria, kelp, seaweed, or yeast can also be utilized to produce a protein rich biomass. These are not the only sources of biomass since biomass from any source can be used that contains desired proteinaceous material of significant nutritional value.

Biomass

Biomass is that biological material derived from (or having as its source) living or recently living organisms. Algal biomass is derived from algae, and microbial biomass is derived from microorganisms. Biomass utilized in the present invention can be derived from any organism or class of organisms, including those described herein. Microbial biomass (e.g., algal biomass) can be harvested from natural waters or cultivated. When cultivated, this can be done in open ponds or in a photobioreactor or fermentation vessels of any appropriate size. The microbes or algae can be either phototrophic or heterotrophic. In some embodiments only light and carbon dioxide are provided but nutrients can be included in any culture medium, for example nitrogen, phosphorus, potassium, and other nutrients. In other embodiments sugars and other nutrients are included in the culture medium.

When sufficient biomass has been generated the biomass can be harvested from cultivation. The harvest can be taken or made into the form of a broth, suspension, or slurry. The biomass can generally be easily reduced by centrifugation to a raw biomass of convenient volume.

Organoleptic Properties

Organoleptic taste and smell properties refers to those properties of a food or food ingredient relating to the sense of taste and/or smell, respectively, particularly with reference to the taste or smell property being pleasing or unpleasant to a human or animal consumer. Methods of evaluating the organoleptic taste and smell properties of foods are known by those of ordinary skill in the art.

Generally these methods involve the use of a panel of several persons, such as an evaluation panel of 4 or 5 or 6 or 7 or 8 or more than 8 persons. The panel is generally presented with several samples (e.g., 3 or 4 or 5 or 6 or 7 or 8 or more than 8 samples) in a "blind" study, such that the panel members do not know the identity of each sample. The panel then rates the samples according to a provided scale, which can have 3 or 4 or 5 or 6 or more than 6 categories describing the taste and/or smell properties of each sample. The findings of a majority of panel members can then be utilized to determine whether a sample has desirable organoleptic properties relative to other samples provided.

One example of such a method of evaluating such properties of food is the 9 point hedonic scale, which is also known as the "degree of liking" scale. (Peryam and Girardot, N. F., *Food Engineering*, 24, 58-61, 194 (1952); Jones et al. *Food Research*, 20, 512-520 (1955)). This method evaluates preferences based on a continuum and categorizations are made based on likes and dislikes of participating subjects. The 9 point method is known to persons of skill in the art, and has been widely used and shown to be useful in the evaluation of food products. One can therefore evaluate whether certain foods have more desirable or less desirable taste and/or smell properties. Both taste and smell properties can be evaluated according to the hedonic scale. In one embodiment the protein food or food ingredient produced by the methods of the present invention scores higher on the 9 point hedonic scale versus protein products from the same source that has not been subjected to one or more steps of the invention. Other methods of evaluating organoleptic taste and/or smell properties can also be utilized.

The specific criteria utilized by an evaluation panel can vary but is related to whether the organoleptic properties of a sample are pleasing or displeasing. Common criteria that can be evaluated include, but are not limited to whether the sample has a smell or taste that is briny (having a salty or salt water character), fishy (having a character related to fish), ammonia-like (having a character related to or resembling ammonia). These can be subjective determinations but people are familiar with these sensations and, when provided to a panel of persons to evaluate, meaningful conclusions are generated.

Certain chemicals that cause the undesirable organoleptic properties are removed by the methods described herein. These chemicals can be one or more of a number of malodorous and/or foul tasting compounds, which in some cases are volatile compounds. Examples of lipidic compounds that can contribute to undesirable organoleptic properties include saturated or unsaturated or polyunsaturated fatty acids (e.g., DHA), which can also be present in an oxidized form (or become oxidized during purification and/or isolation of a protein) and therefore contribute to the undesirable properties of a food or food ingredient.

In some embodiments the compounds that confer undesirable organoleptic properties are lipidic material, which can be covalently bound to desired proteins or otherwise closely associated with the protein content of the material. Lipidic compounds can also be non-covalently but closely associated with the protein in such a way that they cannot be purified way from the protein by conventional purification methods. The chemicals can also be non-lipidic and examples include, but are not limited to dimethylsulfide (DMS), dimethylsulfoniopropionate (DMSP), geosmin, methyl-isoborneol (MIB), and saturated or unsaturated fatty acid moieties. The fatty acid (or fatty acid moieties) can comprise but are not limited to gamma-linolenic acid, alpha-linolenic acid, linoleic acid, stearidonic acid, eicosapentaenoic acid, docosahexaenoic acid (DHA), and arachiconic acid, any ω-3 or ω-6 fatty acid, or any of the aforementioned in an oxidized form. The methods of the invention can reduce the amount of one or more of these compounds in the protein material by at least 20% or at least 30% or at least 40% or at least 50% or at least 70% or at least 80% or at least 90% versus the amount in protein material from the biomass that has not been subjected to a method of the invention. Malodorous and/or foul tasting compounds (organoleptically unacceptable compounds) can also include oxidized lipids (e.g., oxidized unsaturated fatty acids or oxidized omega-3 fatty acids) as well as proteins that can confer the malodorous and/or foul tasting properties. Malodorous and/or foul tasting compounds can also comprise lipidic material covalently bound to or otherwise closely associated with proteins in the proteinaceous material.

Methods

The methods of the invention can comprise any one or more of the following steps. The methods can comprise a step of fermentation of a microbe, such as an algae or microalgae, to form a microbial biomass; one or more steps of lysing and/or homogenization of the cells of the microbial biomass, which can be done by any suitable method (e.g., mechanical homogenization), and can be done in any of the solvents listed herein; one or more steps of delipidation of the microbial biomass, which can be performed in any suitable solvent as described herein and can be done simultaneously with or during the homogenization step; performing one or more steps of an acid wash on the microbial biomass; one or more steps of delipidation or solvent washing of the acid washed biomass; drying of the microbial biomass; optionally passing of the biomass through a particle size classifier; and retrieval of proteinaceous product material. The methods can involve performing the steps in any order, and one or more of the steps can be eliminated. One or more of the steps can be repeated to optimize the yield or quality of protein material from the biomass such as, for example, repetition of one or more delipidation step.

Delipidation and Solvent Washing

In some embodiments the methods involve one or more steps of mechanical homogenization or mixing, which can involve (but is not limited to) bead milling or other high shear mixing (e.g. a ROTOSTAT® mixer) or emulsifying. A homogenization step can be performed for at least 5 minutes or at least 10 minutes or at least 15 minutes or at least 20 minutes. These one or more steps can be followed by or separated by a step of centrifugation and (optionally) re-suspension in a buffer or solvent for an (optional) additional step of homogenization or mixing. Other mechanical stressors include, but are not limited to ultrasonic homogenizers or roto/stator homogenizers.

In one embodiment the biomass is delipidated prior to being subjected to an acid wash. The mechanic stress can be applied with the biomass in contact with an appropriate solvent. Thus, delipidation can involve a lipid extraction or solvent washing step. A solvent washing step involves exposure (or "washing") of the biomass to solvent for an appropriate period of time, which can be at least 5 minutes or at least 10 minutes or at least 15 minutes or about 15 minutes). The solvent can be any appropriate solvent, and in some embodiments is a polar solvent or a polar, protic solvent. Examples of useful polar, protic solvents include, but are not limited to ethanol, formic acid, n-butanol, isopropanol (IPA), methanol, acetic acid, nitromethane, hexane, acetone, water, and mixtures of any combination of them. For example, in one embodiment the solvent can be a combination of hexane and acetone (e.g., 75% hexane and 25% acetone). In another embodiment the solvent in 90% or 100% ethanol. Any suitable ratio of solvent to biomass can be used such as, for example, 5:1, 6:1, 7:1, 8:1, 9:1, and other ratios. But the skilled person will realize other appropriate solvents or combinations that will find use in the invention.

The procedure should ensure proper lysing of the cells comprising the biomass to maximize the protein extraction and make lipidic material available for extraction from the biomass. After mechanical homogenization the biomass can be separated by centrifugation and the lipidic materials in the supernatant removed. One or more additional steps of delipidation or solvent washing with the solvent can be performed to maximize delipidation. In some embodiments a second or subsequent cycle(s) of delipidation can utilize a different solvent than used in the first cycle or in a previous cycle to increase the chances of removing more undesirable compounds. In some embodiments a second solvent can also be included to provide for separation, for example including hexane and/or acetone or another hydrophobic solvent can provide for separation and thus extract more undesirable hydrophobic compounds. After homogenization and at least one solvent washing step (solvent washing can be done simultaneously with homogenization by homogenizing in the presence of solvent) the mixture or biomass can be referred to as a delipidated biomass. The biomass can also have been subjected to mechanical homogenization as a separate step before the solvent washing steps.

Without wishing to be bound by any particular theory it is believed that a large amount of compounds having undesirable organoleptic taste and smell properties are removed in the one or more delipidation or solvent washing step(s) and/or the one or more acid wash step(s) and/or the one or more steps of solvent washing following the one or more acid washing step(s). Additional substances with undesirable organoleptic properties can be removed by repeating any of the steps one or two or three or more than three times. Additional processes described herein can also be performed as one or more steps in the methods of making or synthesizing a protein material. The result of the processes is a material that is high in protein content and derived from biomass.

In various embodiments the protein material prepared according to the invention has a reduced lipid content. In some embodiments the methods of the invention reduce the lipid content of the biomass from more than 10% or more than 8% or more than 7% or more than 6% or more to 5% to less than 5% lipid content or less than 4% lipid content or less than 3% or less than 2% lipid content or less than 1% lipid content, all w/w, present in the protein product material.

Acid Wash

In some embodiments the biomass is subjected to one or more acid wash step(s). In one embodiment the acid wash step is performed on delipidated biomass. Acid washing can comprise exposing the delipidated biomass to acid or a depressed pH for a period of time. The biomass, and therefore the proto-protein it contains, can be exposed to the acid wash in a solution, suspension, slurry, or any suitable state. The acid wash can utilize any suitable inorganic acid (or a suitable organic acid), which are derived from one or more inorganic compounds that form hydrogen ions when dissolved in water. Examples include, but are not limited to, sulfuric acid, nitric acid, phosphoric acid, boric acid, hydrochloric acid, hydrofluoric acid, hydrobromic acid, and perchloric acid. The person of ordinary skill will realize other inorganic acids that also function in the invention. The delipidated biomass can be mixed with water to generate an aqueous mixture. The acid solution (e.g., 1M sulfuric acid) can then be pipetted into the mixture until the pH is reduced to a depressed pH. In various embodiments the pH can be adjusted to a depressed pH of about 4.0 or about 3.8 or about 3.5 or about 3.3 or about 3.2 or about 3.0 or about 2.8 or about 2.5 or from about 2.0 to about 2.5 or from about 2.0 to about 3.0, or from about 2.0 to about 4.0, or from about 2.0 to about 3.5, or from about 2.2 to about 2.8, or from about 2.3 to about 2.7, or from about 2.2 to about 3.8, or from about 2.3 to about 3.7, or from about 2.5 to about 3.0, or from about 2.8 to about 3.2, or from about 3.0 to about 3.5, or from about 3.2 to about 3.8. In other embodiments the pH can be adjusted to less than about pH 4.0 or less than about pH 3.7 or less than about pH 3.6 or less than about pH 3.5 or less than about pH 3.3 or less than about pH 3.0 or less than about pH 2.7 or less than about pH 2.5. The mixture can then be held at the indicated pH for a period of time. The mixture can also be mixed or stirred or incubated for the period of time, or a portion thereof. The period of time can be any of at least 10 minutes or at least 20 min. or at least 30 min, or from about 20 minutes or about 30 minutes, or about 40 minutes, or from 10-30 minutes, or from 10-40 minutes, or from 20-40 minutes, or from 20 minutes to 1 hour, or from 10 minutes to 90 minutes, or from 15 minutes to 45 minutes, or at least 1 hour or about 1 hour or at least 90 minutes or at least 2 hours.

After the biomass has been exposed to the depressed pH for an appropriate period of time (and optional mixing) the pH can then be raised to a raised pH by addition of a basic or alkaline compound, for example KOH. Persons of ordinary skill in the art will realize that other basic or alkaline compounds can also be used, for example sodium hydroxide, calcium hydroxide, or other basic compounds. The basic compound can be added at any convenient concentration, e.g., about 1 M or 0.5-1.5 M or 0.75-1.25M. The basic compound can be added until the pH is adjusted to a raised pH of about 4.5. But in other embodiments the raised pH can be about 4.0 or about 4.2 or about 4.7 or about 5.0. In more embodiments the pH can be raised to greater than 4.0 or greater than 4.2 or greater than 4.5 or greater than 4.7 or greater than 5.0. After the pH adjustment to the raised pH the mixture can be stirred or incubated for an appropriate period of time, which in some embodiments is about 30 min or about 1 hour or about 90 minutes or more than 30 minutes or more than 1 hour.

When the pH is adjusted to the depressed pH there is a noticeable decrease in the viscosity of the mixture from a thick slurry of poor mixing capability to a thin, watery consistency of markedly lower viscosity (i.e. there is an observable decrease in viscosity). The decrease in viscosity can be observed at the start of the acid addition by, for example, the inability of a common laboratory overhead mixer to be able to fully blend the solution (cavitation at the impeller). As the pH is lowered the change in viscosity can be observed as changing to a viscosity similar to a watery solution requiring a reduction in the impeller tipspeed to avoid splashing of the solution. Thus, the change in viscosity can be a decrease of at least 10% or at least 20% or at least 30% or at least 40% or at least 50%, as measured by standard methods of measuring viscosity such as a viscometer. Examples of methods of measuring viscosity include, but are not limited to, a glass capillary viscometer or a vibrating needle viscometer, a rheometer, a rotational rheometer, and the inclined plane test, but any suitable method can be utilized. When the pH is adjusted upwards to the raised pH the viscosity of the mixture increases, but does not achieve its viscosity prior to exposure to acidic conditions, revealing that a marked, irreversible, and permanent chemical change has occurred from the initial protein-containing mixture derived from the biomass.

The acid wash step does not truly hydrolyze the proteins in the biomass, but rather frees lipid moieties from the proteinacious (proto-protein) molecules in the biomass. The step may cause a conformational change in the proteins, and thereby freeing the lipidic moieties and allowing them to be removed. Without wanting to be bound by any particular theory it is believed that subjecting the proto-protein to the delipidation and/or acid wash and/or other processes described herein may free or dissociate bound lipids by making (possibly irreversible) conformational changes in the proto-protein. It may also result in cleavage of covalently bound lipid-protein conjugates. These processes may make the lipid species (or other solvent soluble molecules) available for removal during solvent washing and/or extraction steps. These steps, and possibly in combination with the additional steps described herein, are believed to thus remove the portions of the proto-protein that give the undesirable organoleptic properties, and thus provide the organoleptically acceptable protein-containing material that is the food or food ingredient of nutritional interest in the invention, which is thus harvested. The protein-containing food or food product produced by the processes described herein is thus a markedly different molecule than the proto-protein that begins the processes.

Post-Acid Wash Re-Washing (Re-Working) Steps

Following the acid wash step there can be one or more steps of "reworking" or solvent washing, each optionally followed by a step of centrifugation to achieve a pellet, and resuspension in a solvent. The solvent can be any appropriate solvent as described herein for a solvent washing and/or delipidation step. After the one or more reworking or solvent washing steps (if performed) post acid wash, the protein mixture can be optionally dried in a rotary evaporator to make a protein concentrate, which can be utilized as a food or food ingredient.

Proto-Protein

The biomass contains a proto-protein, which is a protein-containing molecule which also contains a significant non-protein moiety, which can be a lipid moiety. The proto-protein can be the protein produced by the microbe in its natural form, and before being treated according to the methods described herein. The proto-protein is close to its natural form and has undesirable or unfavorable organoleptic taste and smell properties and would score relatively low on the "degree of liking" scale or other method of evaluating organoleptic properties. Various algae and microbes produce proteins with these characteristics, and in some embodiments the proto-protein is an algal protein with undesirable organoleptic properties. In the methods of the invention the proto-protein is converted into the protein-containing food or food ingredient, which has more desirable organoleptic properties and scores higher than the proto-protein on methods of evaluating such properties. In addition to (or instead of) lipid moieties the proto-protein can have other, molecular components or moieties that cause it to have (or worsen) its undesirable organoleptic properties.

The molecular weight distribution of the proto-protein refers to the percentage of proto-protein molecules having a molecular weight within a specified size range or ranges. For example, the proto-protein may have a molecular weight distribution so that at least 50% or at least 60% or at least 70% of the proto-protein molecules (by weight) have a molecular weight of between about 10,000 and about 100,000 daltons, or from about 10,000 to about 50,000 daltons, or from about 20,000 to about 100,000 daltons, or from about 20,000 to about 80,000 daltons, or from about 20,000 to about 60,000 daltons, or from about 30,000 to about 50,000 daltons, or from about 30,000 to about 70,000 daltons. In other embodiments at least 70% or at least 80% of the proto-protein molecules have a molecular weight of between about 10,000 and about 100,000 daltons, or from about 20,000 to about 80,000 daltons, or from about 30,000 to about 50,000 daltons, or from about 30,000 to about 70,000 daltons. In other embodiments the molecular weight distribution of the proto-protein may be such that less than 25% or less than 10% or less than 5% of the proto-protein molecules have a molecular weight below about 20,000 daltons or below about 15,000 daltons or below about 10,000 daltons.

The methods of the invention convert a biomass containing a proto-protein into a proteinaceous or protein-rich concentrate. The fatty acid methyl ester (FAME) profile of the biomass at various steps can be evaluated to determine the quantity of lipidic material removed during the processes. Table 1 and FIG. 1 show the percent removal of FAME by the processing steps of the invention.

TABLE 1

Percent removal of FAME by processing steps

| | Process Step | | | |
|---|---|---|---|---|
| Sample ID | First Bead Milling | Second Bead Milling | Acid Wash | Final |
| 505-002 | — | 25% | 26% | 59% |
| 506-002 | 19% | 34% | 21% | 79% |
| 514-002 | 8% | 50% | 24% | 80% |
| average | 13.5% | 33% | 24% | |

The values in Table 1 reflect the percent of lipid removed by the indicated process step from the input material at that step. "Final" indicates the percent of total lipid removed versus the lipid content of the starting biomass. The data corresponds to the graph in FIG. 3. In various embodiments at least 60% or at least 70% or at least 75% of the lipid content in the fermented biomass that begins the methods is removed by the methods of the invention.

In some embodiments the biomass (or proto-protein) has a % FAME of greater than 9% or greater than 10% or greater than 11% or greater than 12% or greater than 13%. As a result of the methods described herein the % FAME can be reduced to less than 5% or less than 4% or less than 3% or less than 2% or less than 1%.

The para-anisidine test (pAV), which is a standard test for secondary oxidation products of lipids, can also be used to monitor the amount of secondary oxidation products of lipids present after the processes of the invention, and therefore further characterize the protein product produced by the methods of the invention. In some embodiments the protein product produced by the methods of the invention has a pAV value of less than 2.0 or less than 1.0 or less than 0.9 or less than 0.8 or less than 0.7 or less than 0.6 or less than 0.5.

More Methods

In some embodiments the invention provides methods of increasing the protein content of a biomass. In some embodiments the product of the invention is a protein-containing product having a higher protein concentration than the original biomass, with neutral color and improved hedonic properties. In various embodiments the protein-containing biomass that enters the processes of the invention can have a protein content of less than 65% or 50-65% or 40-70% or 45-65% or 45-70% (all w/w) and the protein content of the product of the methods is raised to greater than 65% or greater than 68% or greater than 70% or greater than 72% or greater than 75% or greater than 77% or greater than 80% or 70-90% or 65-90% or 70-90% or 72-87% or 75-85% or 75-80%.

The invention also provides methods of lowering the arginine and glutamic acid (or glutamic acid and glutamine) content of a protein material. Arginine and glutamic acid (and glutamine) are two amino acids that are generally easy to find in various types of food products. In many embodiments it is desirable to have a protein-rich food or food product that has a lower content of these common amino acids so that a more balanced supply of the 20 essential amino acids can be obtained in a food or food ingredient. The methods of the invention produce a protein product with a lower amount of glutamic acid (or glutamic acid and glutamine) and arginine. In various embodiments the percent of glutamic acid (or glutamic acid and glutamine) is lowered from more than 21% or more than 22% to less than 20% or less than 19% (% of total amino acids). The percent of arginine is lowered from more than 9% to less than 9% (% of total amino acids) The methods of lowering the arginine and glutamic acid (or glutamic acid and glutamine) content comprise any of the methods described herein.

Example 1

This example provides a general scheme for producing a powder containing a proto-protein from an algal source. This example illustrates a specific method but persons of ordinary skill with resort to this disclosure will realize other embodiments of the methods, as well as that one or more of the steps included herein can be eliminated and/or repeated.

In this example the algae used were chytrids of the genus *Aurantiochytrium* sp., which were cultivated in a fermenter containing a marine medium containing 0.1 M glucose and 10 g/L of yeast extract (or peptone substitute), which supplied a source of organic carbon. The medium also contained macronutrients, including 0.1M NaCl, 0.01M $CaCl_2$, 0.04M $Na_2SO_4$, 0.03M $KH_2PO_4$, 0.04M $(NH_4)_2SO_4$, 0.006M KCl, 0.02M $MgSO_4$), plus nanomolar quantities of vitamin B12, thiamine and biotin. The culture was maintained at 30 C for 24 hours with 300-80 rpm of agitation, 0.1 vvm to 1.0 vvm aeration, 50% dissolved oxygen, and pH controlled to 6.3±0.1 using 30% NaOH. After harvesting, the fermentation broth was removed from the cells via centrifugation and the resulting biomass pellet is diluted in water and re-centrifuged (cell wash). The resulting paste was mixed with antioxidants to prevent oxidation of oils and other components, and then drum dried to remove water, which produced a dry cellular material. The dry cells were then thoroughly lysed in 100% ethanol in a bead mill. The solvent removes soluble substances such as lipids, and the delipidated biomass is separated from the miscella using centrifugation. The biomass was then subjected to an acid wash via titration of 1 N $H_2SO_4$, until the pH was acidified to about 3.5. The biomass was then mixed for 30 minutes. The pH was then raised to about 4.5 with 1 N NaOH and the biomass mixed for 1 hour.

The acid washed material was then centrifuged and the supernatant removed. The pellet was then subjected to two rework steps, which involved two rounds of suspension in 100% ethanol followed by high shear mixing and centrifugation. The supernatant was decanted to maximize extraction and removal of undesired compounds. The high shear mixing was performed with a rotor stator type mixer (e.g., IKA ULTRATORRAX®) with the temperature being controlled at <20° C. by an ice bath. The resultant ethanol-washed pellet (biomass) was then dried by placing in a modified rotary evaporation flask to promote tumble-drying at room temperature under moderate vacuum. After approximately 4 hours the material changed from a paste to a powder. At this point, the material was removed from the rotary evaporator and ground to a fine powder with a mortar and pestle. This material was then placed on an aluminum tray in a vacuum oven at 90° C. for approximately 11 hours to remove any residual solvent or moisture. Once dry, the material was passed through a particle size classifier to remove particles greater than 300 um in size. These particles can be completely removed from the final product if desired, or further ground up and returned back to the final product. The end result of the process was a uniform, neutral colored powder of neutral hedonic character, which can be packaged under nitrogen and stored in a −80° C. freezer.

Example 2

Three independent fermentations were performed on chytrids of the genus *Aurantiochyrium* sp. in rich medium similar to that of Example 1 and the mass of the acid wash supernatant stream was quantitated, and protein determined by the Dumas method (quantitative determination of Nitrogen by elemental analysis). As shown in Table 2 below, the acid wash removed between 8.8% and 15.8% of the initial feedstock mass. Converting nitrogen content to protein content by the calculation (N*6.25) estimates the protein content of the acid wash solids is 12.15% to 15.50% protein. The protein removed by the acid wash step ranged from 2.01% to 3.4% of the initial protein in the feed.

TABLE 2

Acid Wash Supernatant Masses and Protein

|  | Sample 825 | Sample 908 | Sample 319 |
|---|---|---|---|
| Mass removed, % of feed | 15.80% | 14.00% | 8.80% |
| Acid wash Solids % protein | 12.60% | 12.15% | 15.50% |
| Protein, % of feed Protein | 3.40% | 2.70% | 2.01% |

Example 3

An additional example of the impact of the acid wash upon amino acid composition is shown below. Two separate processes were performed where the acid wash supernatant was dialyzed and dried, and analyzed for amino acid composition. An *Aurantiochytrium* chytrid strain (#533) was processed as described above, the acid wash supernatant and algal protein concentrate were analyzed and compared to the initial dry biomass feed. It was found that glutamic acid (or glutamic acid and glutamine) and arginine are selectively removed from the biomass during the acid wash.

Without wanting to be bound by any particular theory it is believed that the acid wash step prepares the proteinaceous material for a preferential protein removal so that the content of generally unwanted amino acids (arginine, glutamic acid (or glutamic acid and glutamine), hydroxyproline) is lowered in the final protein produce versus the raw algal protein. After acid washing the samples were subjected to two additional rounds of solvent washing. It is also believed that the acid wash step exposes or otherwise renders certain proteins in the proteinaceous material susceptible to removal, and these removed proteins are high in the content of these unwanted amino acids. The content of arginine and glutamic acid (or glutamic acid and glutamine) and hydroxyproline is measured by calculating the ratio of each amino acid in the final protein product pellet versus the content in the supernatant. Thus a low ratio indicates the amino acid is more prevalent in the supernatant. Table 3 below illustrates the data and shows that the ratio for these three amino acids is less than 2 or less than 1 or less than 0.75 for arginine, less than 2 or less than 1 or less than 0.75 or less than 0.60 for glutamic acid (or glutamic acid and glutamine), and less than 2 or less than 1 or less than 0.75 or less than 0.55 for hydroxyproline.

TABLE 3

| Amino Acid % of sample | Normalized Acid Wash Supernatant | Normalized Final Product in Pellet | Ratio of Pellet to AWS normalized amino acid composition |
|---|---|---|---|
| Methionine | 0.08% | 0.83% | 10.35 |
| Cystine | 0.13% | 0.48% | 3.80 |
| Lysine | 0.76% | 4.38% | 5.76 |
| Phenylalanine | 0.01% | 2.82% | 315.04 |
| Leucine | 0.21% | 4.56% | 21.26 |
| Isoleucine | 0.19% | 2.33% | 12.40 |
| Threonine | 0.50% | 3.07% | 6.13 |
| Valine | 0.33% | 3.66% | 11.07 |
| Histidine | 0.35% | 1.76% | 5.04 |
| Arginine | 15.61% | 11.12% | 0.71 |
| Glycine | 0.95% | 3.23% | 3.40 |
| Aspartic Acid | 1.17% | 6.86% | 5.86 |
| Serine | 0.57% | 3.27% | 5.71 |
| Glutamic Acid | 76.24% | 41.97% | 0.55 |
| Proline | 0.35% | 2.64% | 7.58 |
| Hydroxyproline | 0.05% | 0.03% | 0.49 |
| Alanine | 1.70% | 4.20% | 2.48 |
| Tyrosine | 0.72% | 2.27% | 3.18 |
| Tryptophan | 0.09% | 0.79% | 8.87 |
| TOTAL: | 100.00% | 100.00% | 1.00 |

Example 4

Lipid Removal During Acid Wash

Two processes using the same biomass source (chytrid #705) were performed to look at the effect of the acid wash on FAME content in the protein concentrate. After drum drying the initial biomass from the fermenter the samples were subjected to two rounds of mechanical homogenization by bead milling followed by a step of solvent washing in 100% isopropyl alcohol. Sample 225-002/A was subjected to an acid washing step as describe in Example 1 while sample 225-002/A.2 was not. Each sample was then subjected to two reworking solvent washing steps in 100% isopropyl alcohol before being dried in a rotary evaporator. The results clearly show the lowering of the final FAME content in the protein product from 2.19% of final dry weight to 0.89% of final dry weight, which can be attributable to the acid washing step.

TABLE 4

| Lot Designation | Experimental Descriptor | Sample Descriptor | % Protein (Dumas) | Protein concentrate FAME % of dry weight |
|---|---|---|---|---|
| 225-002/A | Acid Washed | Drum Dry/IPA Mill/AW/ Rework/Drying | 83.66% | 0.89% |
| 225-002/A.2 | Non-Acid Washed | Drum Dry/IPA Mill/Rework/ Drying (No acid wash) | 81.22% | 2.19% |

The stepwise efficiency of removing available lipids through the process was examined in order to see the specific contribution of the acid wash step for the removal of lipids. FIG. 1 shows the results for three independent treatments performed using strain #533 in a defined medium. Ethanol was used as the solvent prior to and after the acid wash. The acid wash step included a first adjustment to pH 3.5 with 1 N H$_2$SO$_4$ per Example 1, followed by adjustment to pH 4.5 with 1 N KOH. For each significant process step, the resultant solids were analyzed for FAME content and a percent of available FAME that was removed in the step was calculated, as shown in FIG. 1. The acid wash step removed 26%, 21%, and 24% of the lipid present in the biomass after the bead mill processing (samples 505-002, 506-002, and 514-002, respectively). The data show that when an acid wash step is included in the preparation method the percent of FAME in the protein produce produced is reduced 0.89%, or to less than 1%. When the acid wash step is omitted from the process the percent FAME in the protein produce is 2.19%, or higher than 2%.

Example 5

The para-anisidine test (pAV), which is a standard test for secondary oxidation products of lipids, was used to monitor the amount of secondary oxidation products of lipids present after certain steps of the methods. The pAV values were determined for four independently-fermented batches of chytrid biomass, tested at three steps in the downstream processing: water-washed biomass collected immediately at the conclusion of fermentation (washed pellet); pasteurized biomass; final protein concentrate (after acid washing and two re-working steps). The downstream process steps are shown in the process flow diagram of FIG. 1b and described in Table 5 below.

TABLE 5

| pAV Relative to Soy Protein | | | |
| --- | --- | --- | --- |
| p-AV relative to soy protein | Washed Pellet | Pasteurized Biomass | Protein Concentrate |
| IP-150505-002 | 4.0 | 4.0 | 0.8 |
| IP-150506-002 | 3.6 | 5.4 | 0.5 |
| IP-150511-002 | 3.5 | 2.5 | 0.8 |
| IP-150514-002 | 1.6 | 1.5 | 0.4 |

The values shown in Table 5 are ratios of the pAV of the algal protein concentrate relative to the pAV value determined for a commercially available protein isolate produced from soybean (which is used as a benchmark standard). The data show that prior to the processing steps of bead milling/ethanol extraction and acid washing, the algal protein concentrate has a higher content of secondary lipid oxidation products than does a soybean protein isolate. But after two bead milling/ethanol solvent washing steps and one acid washing step with two reworking solvent washing steps, each of the four samples of protein product have a lower content of secondary lipid oxidation products than the soybean protein isolate. Thus, the steps of the invention, including the acid washing, improve the quality of the protein concentrate with respect to lipid content (and therefore lipid oxidation) and organoleptic properties.

Example 6

Sensory Panels

Reports from sensory panels composed of persons selected to evaluate the organoleptic properties of the protein composition have demonstrated the process results in improved organoleptic (hedonic) character. The presence of an unpleasant fishy odor or taste, or ammonia-like odor or taste, was markedly decreased as a result of the process while the protein material maintained a high protein content.

Persons of ordinary skill in the art understand how to assemble a sensory evaluation panel and evaluate food samples in a reliable manner, for example the 9 point hedonic scale, which is also known as the "degree of liking" scale can be utilized. (Peryam and Girardot, N. F., *Food Engineering*, 24, 58-61, 194 (1952); Jones et al. *Food Research*, 20, 512-520 (1955)). This example therefore provides only one scientifically valid manner of performing such evaluation.

A panel of six adult subjects (3 male and 3 female) evaluate the organoleptic taste and/or smell properties of eight protein products derived from chytrid biomass. The subjects are randomly assigned an identifying letter A-F. Four of the eight samples are prepared according to the procedure of Example 1, which includes one acid wash procedure ("test" samples). The other four samples are control samples, which have been prepared identically except they were not subjected to the acid washing step ("control" samples). After the samples are dried and obtained in powdered form, 1 gram of protein powder is dissolved in deionized water to make a 10% solution in a plastic tube. The eight samples are provided to each subject in random order and without any subject knowing the identity of any sample.

The samples are evaluated for whether the samples are organoleptically pleasing or unpleasant. The subjects are asked to consider "fishy taste and/or smell" and "ammonia-like taste and/or smell" according to the following five category scale: 0—none; 1—slight; 2—moderate; 3 high; and 4—extreme. The subjects are instructed to assign the sample the lowest rating received in either category. The manner of testing is first to evaluate the aroma of the sample. If the subject rates the aroma a 3 or 4 the sample is considered organoleptically unpleasant and no tasting is required. If the aroma rates between 0 and 2 the subject further tests the sample by the "sip and spit" method, with sample being held in the mouth for 1-2 seconds.

In the aroma evaluation portion of the study, 5 of the 6 panel members rate all four control samples a 3, i.e., high fishy smell and high ammonia-like smell. Therefore these 5 subjects do not proceed to the taste portion of the study for these samples and the samples are rated as having unpleasant organoleptic properties. The sixth subject rates three of the four control samples a "3", and the remaining control sample a "2." For the fourth control sample the sixth subject proceeds to the taste portion and rates the remaining control sample a 3.

For the four test samples in the aroma portion of the study, 4 of the 6 subjects rate three of the samples a "0" and one of the samples a "1". The remaining two subjects rate all samples a "0." The subjects then proceed to the taste portion. Four of the subjects rate the samples a "1" and two of the subjects rate the samples a "0". For the taste portion of the study, 4 of the 6 subjects rate the taste of all four samples a "1." The remaining two subjects rate two samples a "0" and two samples a "1."

The data are summarized in Table 6 and show that the protein-containing food or food ingredient prepared according to the present invention has improved organoleptic properties than samples prepared according to traditional methods.

TABLE 6

| Samples Evaluated as either organoleptically pleasing or unpleasant | | | | | | |
|---|---|---|---|---|---|---|
| | A | B | C | D | E | F |
| 1 test | S-0 | S-0 | S-0 | S-0 | S-0 | S-0 |
| | T-1 | T-1 | T-0 | T-1 | T-1 | T-1 |
| 2 test | S-1 | S-0 | S-0 | S-1 | S-0 | S-1 |
| | T-1 | T-1 | T-0 | T-1 | T-1 | T-1 |
| 3 test | S-0 | S-0 | S-0 | S-0 | S-1 | S-0 |
| | T-0 | T-0 | T-1 | T-1 | T-1 | T-1 |
| 4 test | S-0 | S-0 | S-0 | S-0 | S-0 | S-0 |
| | T-0 | T-0 | T-1 | T-1 | T-1 | T-1 |
| 5 control | S-3 | S-3 | S-3 | S-3 | S-3 | S-3 |
| 6 control | S-3 | S-2 T-3 | S-3 | S-3 | S-3 | S-3 |
| 7 control | S-3 | S-3 | S-3 | S-3 | S-3 | S-3 |
| 8 control | S-3 | S-3 | S-3 | S-3 | S-3 | S-3 |

The invention claimed is:

1. A method of making a food product comprising:
   a) delipidating a biomass from an organism that contains a proto-protein, wherein the organism is selected from the group consisting of *Aurantiochytrium, Botryochytrium, Japanochytrium, Oblongochytrium, Schizochytrium,* and *Thraustochytrium;*
   b) subjecting the delipidated biomass to an acid wash at a pH of about 3.5 followed by an adjustment of the pH to about 4.5, to convert the proto-protein into the protein material having a protein content of at least 70% w/w and a fatty acid methyl ester content of less than about 5%, followed by suspension in ethanol; and
   c) identifying protein material with a content of secondary lipid oxidation characterized by a para-anisidine test value (pAV) of less than about 2.0, thereby making the food product.

2. The method of claim 1 wherein the food product is selected from the group consisting of: a breakfast cereal, a snack bar, a soup or stew, a nutrition bar, a binder for bulk artificial meats, an artificial cheese.

3. The method of claim 1 wherein the protein material has a fatty acid methyl ester content of less than 1%.

4. The method of claim 1, wherein the acid wash at pH 3.5 is for at least about 30 minutes and/or the adjustment of the pH to about 4.5 is for at least about 30 minutes.

* * * * *